(12) United States Patent
Yu et al.

(10) Patent No.: US 10,730,049 B2
(45) Date of Patent: Aug. 4, 2020

(54) MICROFLUIDIC CHIP, APPARATUS FOR ENRICHING CELLS AND METHOD FOR ENRICHING CELLS IN A MICROFLUIDIC CHIP

(71) Applicant: MiCareo Taiwan Co., Ltd., Taipei (TW)

(72) Inventors: Hui-Min Yu, Taipei (TW); Wen-Feng Chung, Taipei (TW); Jui-Lin Chen, Taipei (TW)

(73) Assignee: MiCareo Taiwan Co., Ltd., Taipei (TW)

( * ) Notice: Subject to any disclaimer, the term of this patent is extended or adjusted under 35 U.S.C. 154(b) by 163 days.

(21) Appl. No.: 15/975,794

(22) Filed: May 10, 2018

(65) Prior Publication Data

US 2018/0326419 A1 Nov. 15, 2018

Related U.S. Application Data

(60) Provisional application No. 62/504,129, filed on May 10, 2017.

(51) Int. Cl.
*B01L 3/00* (2006.01)
*C12M 3/00* (2006.01)
(Continued)

(52) U.S. Cl.
CPC ....... *B01L 3/502761* (2013.01); *C12M 27/00* (2013.01); *G01N 15/1056* (2013.01);
(Continued)

(58) Field of Classification Search
CPC ... C12M 23/42; C12M 23/40; B01L 3/502769
See application file for complete search history.

(56) References Cited

U.S. PATENT DOCUMENTS

2005/0207940 A1 9/2005 Butler et al.
2007/0029257 A1 2/2007 Mueth et al.
(Continued)

FOREIGN PATENT DOCUMENTS

JP 2003529076 9/2003
JP 2003532400 11/2003
(Continued)

OTHER PUBLICATIONS

"Office Action of Japan Counterpart Application", dated May 14, 2019, p. 1-p. 5.
(Continued)

*Primary Examiner* — Nathan A Bowers
(74) *Attorney, Agent, or Firm* — JCIPRNET

(57) ABSTRACT

In accordance with an embodiment, a microfluidic chip including a first cells enrichment system and a second cells enrichment system is provided. Channel layouts of the first and the second cells enrichment systems are symmetric with respect to a reflection plane vertical to the microfluidic chip. Each of the first the second cells enrichment systems includes a first fluid channel, a second fluid channel, a sample channel, an inlet channel, and a filtration chamber. The sample channel of the first cells enrichment system has a first inner wall and a first outer wall. The sample channel of the second cells enrichment system has a second inner wall and a second outer wall. The first outer wall and the second outer wall are both far from the reflection plane. A distance between the first outer wall and the second outer wall is in the range from about 10 μm to about 1 cm.

16 Claims, 9 Drawing Sheets

(51) Int. Cl.
*C12M 1/02* (2006.01)
*G01N 15/10* (2006.01)
*G01N 15/14* (2006.01)

(52) U.S. Cl.
CPC .............. *B01L 2200/0636* (2013.01); *B01L 2200/0652* (2013.01); *B01L 2200/141* (2013.01); *B01L 2300/0681* (2013.01); *B01L 2300/0816* (2013.01); *B01L 2300/0861* (2013.01); *B01L 2400/0463* (2013.01); *G01N 15/1459* (2013.01); *G01N 2015/1006* (2013.01); *G01N 2015/1081* (2013.01); *G01N 2015/149* (2013.01)

(56) References Cited

U.S. PATENT DOCUMENTS

2010/0028928 A1* 2/2010 Levchenko ............ B01L 3/5025
435/29

2014/0273179 A1 9/2014 Sharpe et al.
2015/0316555 A1 11/2015 Fuchs et al.

FOREIGN PATENT DOCUMENTS

| | | |
|---|---|---|
| JP | 2005521425 | 7/2005 |
| JP | 2006517029 | 7/2006 |
| JP | 2010525325 | 7/2010 |
| JP | 2015051008 | 3/2015 |
| JP | 2016527494 | 9/2016 |
| WO | WO 2015002975 A1 * | 1/2015 |

OTHER PUBLICATIONS

"Search Report of Europe Counterpart Application", dated Jun. 8, 2018, p. 1-p. 10.

* cited by examiner

MICROFLUIDIC CHIP, APPARATUS FOR ENRICHING CELLS AND METHOD FOR ENRICHING CELLS IN A MICROFLUIDIC CHIP

CROSS-REFERENCE TO RELATED APPLICATION

This application claims the priority benefit of U.S. provisional application Ser. No. 62/504,129, filed on May 10, 2017. The entirety of the above-mentioned patent application is hereby incorporated by reference herein and made a part of this specification.

BACKGROUND

Technical Field

The disclosure is related to the technique of enriching a target in a fluid sample, and particularly, related to a microfluidic chip, an apparatus for enriching cells and a method for enriching cells in a microfluidic chip.

Description of Related Art

A microfluidic chip is a chip-like device having one or more micro flow channel allowing a fluid sample and/or a required reagent travelling therein, such that the fluid sample may be tested in the channel of the microfluidic chip. The microfluidic chip has been used in various field, particularly, the bio-related field such as the biomedical, biochemical, or related field. In the application of the bio-related field, a blood sample is tested in the microfluidic chip. Usually, a blood sample contains various cells therein, and the need to sort rare cells is rapidly expanding. The rare target cells population includes circulating tumor cells (CTCs), hematopoietic stem cells (HSCs), and circulating fetal cells (CFCs) from blood. However, the commercial cell sorter has some limitation regarding sorting the rare cells population, including generally low selectivity, significant sample loss, and high operating pressures could result in a loss of function or viability for further analysis. To address these needs, researchers are looking toward microfluidic devices as the platform for the rare cells sorting. Therefore, a microfluidic chip capable of improving the test efficiency is required.

SUMMARY

The disclosure is directed to a microfluidic chip capable of running two fluid samples.

The disclosure is also directed to an apparatus for enriching cells capable of enriching two fluid samples simultaneously.

The disclosure is further directed to a method for enriching cells in a microfluidic chip capable of enriching two fluid samples simultaneously.

According to an embodiment, a microfluidic chip includes a first cells enrichment system and a second cells enrichment system. A channel layout of the first cells enrichment system and a channel layout of the second cells enrichment system are symmetric with respect to a reflection plane vertical to the microfluidic chip. Each of the first cells enrichment system and the second cells enrichment system includes a first fluid channel, a second fluid channel, a sample channel positioned between the first fluid channel and the second fluid channel, a waste channel, an inlet channel, and a filtration chamber reached by the inlet channel. The first fluid channel, the second fluid channel and the sample channel converge at a first side of a confluence chamber, the waste channel and the inlet channel diverge from a second side of the confluence chamber, and the first side and the second side are opposite sides. The inlet channel forms a fluid communication between the filtration chamber and the confluence chamber. The sample channel of the first cells enrichment system has a first inner wall and a first outer wall, the sample channel of the second cells enrichment system has a second inner wall and a second outer wall, the first outer wall and the second outer wall are both far from the reflection plane, and a distance between the first outer wall and the second outer wall is in the range from about 10 μm to about 1 cm.

According to an embodiment, the distance between the first outer wall and the second outer wall is in the range from about 700 μm to about 1200 μm.

According to an embodiment, the microfluidic chip further includes a reagent inlet and a reagent channel. The reagent channel bifurcates in a first branch and a second branch, wherein the first branch is in fluid communication with the filtration chamber of the first cells enrichment system, and the second branch is in fluid communication with the filtration chamber of the second cells enrichment system.

According to an embodiment, each of the first branch and the second branch of the reagent channel includes an anti-contamination section with a plurality of filter slits arranged therein.

According to an embodiment, the reagent channel further includes a bubble trapping chamber before bifurcating in the first branch and the second branch.

According to an embodiment, each of the first cells enrichment system and the second cells enrichment system further includes a waste outlet hole passing through an outer surface of the microfluidic chip and in fluid communication with the waste channel.

According to an embodiment, each of the first cells enrichment system and the second cells enrichment system further includes a filtration wall disposed within the filtration chamber and splitting the filtration chamber into a first sub-chamber and a second sub-chamber. The filtration wall includes a plurality of through slits and a roof-like structure. Each of the plurality of through slits crosses through the filtration wall to form a fluid communication between the first sub-chamber and the second sub-chamber. The roof-like structure is arranged at a side of the filtration wall facing the first sub-chamber, wherein the roof-like structure defines a blocking edge and a recess indented from the blocking edge.

According to an embodiment, each of the first cells enrichment system and the second cells enrichment system further includes an outlet channel departing from the second sub-chamber.

According to an embodiment, each of the first cells enrichment system and the second cells enrichment system further includes an outlet hole passing through an outer surface of the microfluidic chip and in fluid communication with the outlet channel.

According to an embodiment, each of the first cells enrichment system and the second cells enrichment system further includes a sample inlet hole, a first buffer inlet hole, a second buffer inlet hole, and a buffer switching hole. The sample inlet hole passes through an outer surface of the microfluidic chip and in fluid communication with the sample channel. The first buffer inlet hole passes through the outer surface of the microfluidic chip and in fluid communication with the first fluid channel. The second buffer inlet hole passes through the outer surface of the microfluidic chip and in fluid communication with the second fluid channel. The buffer switching hole passes through the outer surface of the microfluidic chip and in fluid communication with the second fluid channel between the second buffer inlet hole and the confluence chamber.

According to an embodiment, an apparatus for enriching cells includes a microfluidic chip including a first cells enrichment system and a second cells enrichment system, two switches, a cell detector and a processor. Each of the first cells enrichment system and the second cells enrichment system includes a first fluid channel; a second fluid channel; a sample channel positioned between the first fluid channel and the second fluid channel; a waste channel; an inlet channel; and a filtration chamber reached by the inlet channel. The first fluid channel, the second fluid channel and the sample channel converge at a first side of a confluence chamber, the waste channel and the inlet channel diverge from a second side of the confluence chamber, and the first side and the second side are opposite sides. The inlet channel forms a fluid communication between the filtration chamber and the confluence chamber. The switches are respectively connected to the second fluid channel of the first cells enrichment system and the second fluid channel of the second cells enrichment system. The cell detector has a view field. The cell detector is configured to detect a target cell within the sample channels of the first cells enrichment system and the second cells enrichment system. The processor is configured to independently control the two switches in response to a detection result of the cell detector, wherein the processor, upon detection of the target cell within the sample channel of one of the first cells enrichment system and the second cells enrichment system, activates the corresponding switch connected to the one of the first cells enrichment system and the second cells enrichment system.

According to an embodiment, a first buffer supply is further in fluid communication with the first fluid channel of each of the first cells enrichment system and the second cells enrichment system and a second buffer supply is further in fluid communication with the second fluid channel of each of the first cells enrichment system and the second cells enrichment system. The corresponding switch is connected between the second buffer supply and the second fluid channel of each of the first cells enrichment system and the second cells enrichment system. The processor is further configured to control the second buffer supply to form a buffer flow in the second fluid channel in each of the first cells enrichment system and the second cells enrichment system, and the buffer flow directs a sample fluid from the sample channel to enter the waste channel at the confluence chamber. The processor, upon detection of the target cell, activates the corresponding switch to adjust the buffer flow, and the adjusted buffer flow directs the sample fluid from the sample channel to enter the inlet channel at the confluence chamber.

According to an embodiment, a method for enriching cells by using aforementioned microfluidic chip comprising a first cells enrichment system and a second cells enrichment system includes the following steps. Each of the first cells enrichment system and the second cells enrichment system includes a first fluid channel; a second fluid channel; a sample channel positioned between the first fluid channel and the second fluid channel; a waste channel; an inlet channel; and a filtration chamber reached by the inlet channel. The first fluid channel, the second fluid channel and the sample channel converge at a first side of a confluence chamber, the waste channel and the inlet channel diverge from a second side of the confluence chamber, and the first side and the second side are opposite sides. The inlet channel forms a fluid communication between the filtration chamber and the confluence chamber. A first buffer fluid is supplied to the first fluid channel and a second buffer fluid is supplied to the second fluid channel of the first cells enrichment system. A first sample fluid containing target cells is injected to the sample channel of the first cells enrichment system. The second buffer flow in the second fluid channel of the first cells enrichment system is controlled to direct the second sample fluid from the sample channel of the first cells enrichment system to enter the inlet channel of the first cells enrichment system upon detection of a target cell within the sample channel of the first cells enrichment system. Otherwise, the second buffer flow in the second fluid channel of the first cells enrichment system is controlled to direct the first sample fluid to enter the waste channel of the first cells enrichment system.

According to the present invention, the second cells enrichment system has the similar layout design with the first cells enrichment system. Therefore, the second cells enrichment system follows the same enrichment process with the first cells enrichment system correspondingly. According to an embodiment, the controlling of the second buffer flow in the second fluid channel of the second cells enrichment system is independent from the controlling of the second buffer flow in the second fluid channel of the first cells enrichment system.

In view of the above, a microfluidic chip in accordance with some embodiment includes two cells enrichment system so that the microfluidic chip can be used for analyzing two samples simultaneously, which improves the efficiency of enriching cells.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
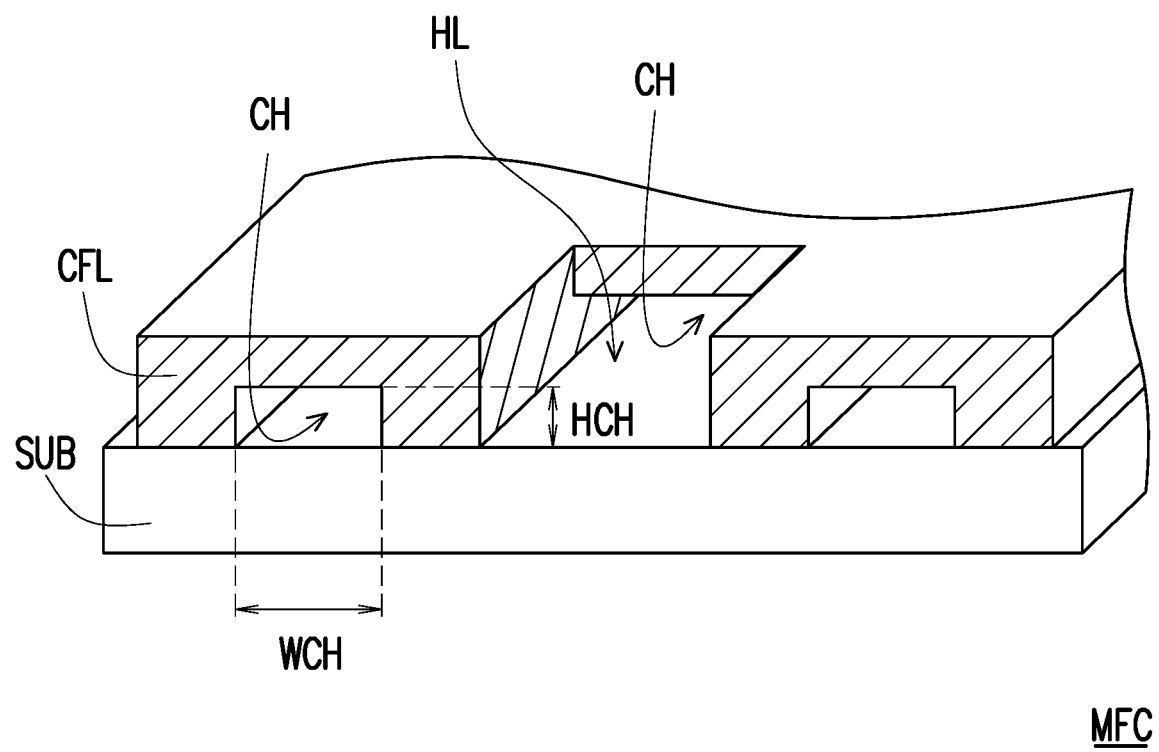
FIG. 1 schematically illustrates a perspective view of a portion of a microfluidic chip in accordance with an embodiment.

FIG. 1 schematically illustrates a perspective view of a portion of a microfluidic chip in accordance with an embodiment. Referring to FIG. 1, a microfluidic chip MFC may include a substrate SUB and a channel forming layer CFL. The channel forming layer CFL may be bonded to the substrate SUB via plasma bonding process or other process capable of firmly adhering the channel forming layer CFL to the substrate SUB. The channel forming layer CFL may have specific patterns and the patterns of the channel forming layer CFL defines one or more channel CH and one or more hole HL based on a desired design. The patterns defining the channel CH may be concave-like patterns and the channel forming layer CFL is bonded to the substrate SUB to form a sealed space at the channel CH allowing a fluid travelling therein. The patterns defining the hole HL may pass through the whole thickness of the channel forming layer CFL and one end of the hole HL may be exposed after the channel forming layer CFL is bonded to the substrate SUB. In other words, the hole HL is a structure passing through the outer surface of the microfluidic chip MFC. Specifically, one hole HL may be adjoined to one corresponding channel CH to construct a desired channel layout, in which the hole HL is used for forming a fluid communication between the channel CH and an external device or environment. The channel forming layer CFL may be made of a moldable and elastic material such as polydimethylsiloxane (PDMS), or the like and may be molded to have the patterns defining the required channels CH and holes HL by lithography replication or other alternative process. The substrate SUB may be a transparent substrate having sufficient rigidity to support the channel forming layer CFL. A material of the substrate SUB may be glass or other material having sufficient rigidity and transparency. However, the disclosure is not limited thereto and the microfluidic chip MFC may be formed by other method. For example, in some embodiments, the channel forming layer CFL may be formed integrally with the substrate SUB. That is, the channel forming layer CFL may be made of the same material as the substrate SUB and there may be no junction between the channel forming layer CFL and the substrate SUB. In some embodiments, the width WCH of the channel CH may be in a range of 50 μm to 500 μm and the height HCH of the channel CH may be in a range of 40 μm to 50 μm. In addition, the layout of the channel CH may arrange based on the design requirement.

Figure 2:
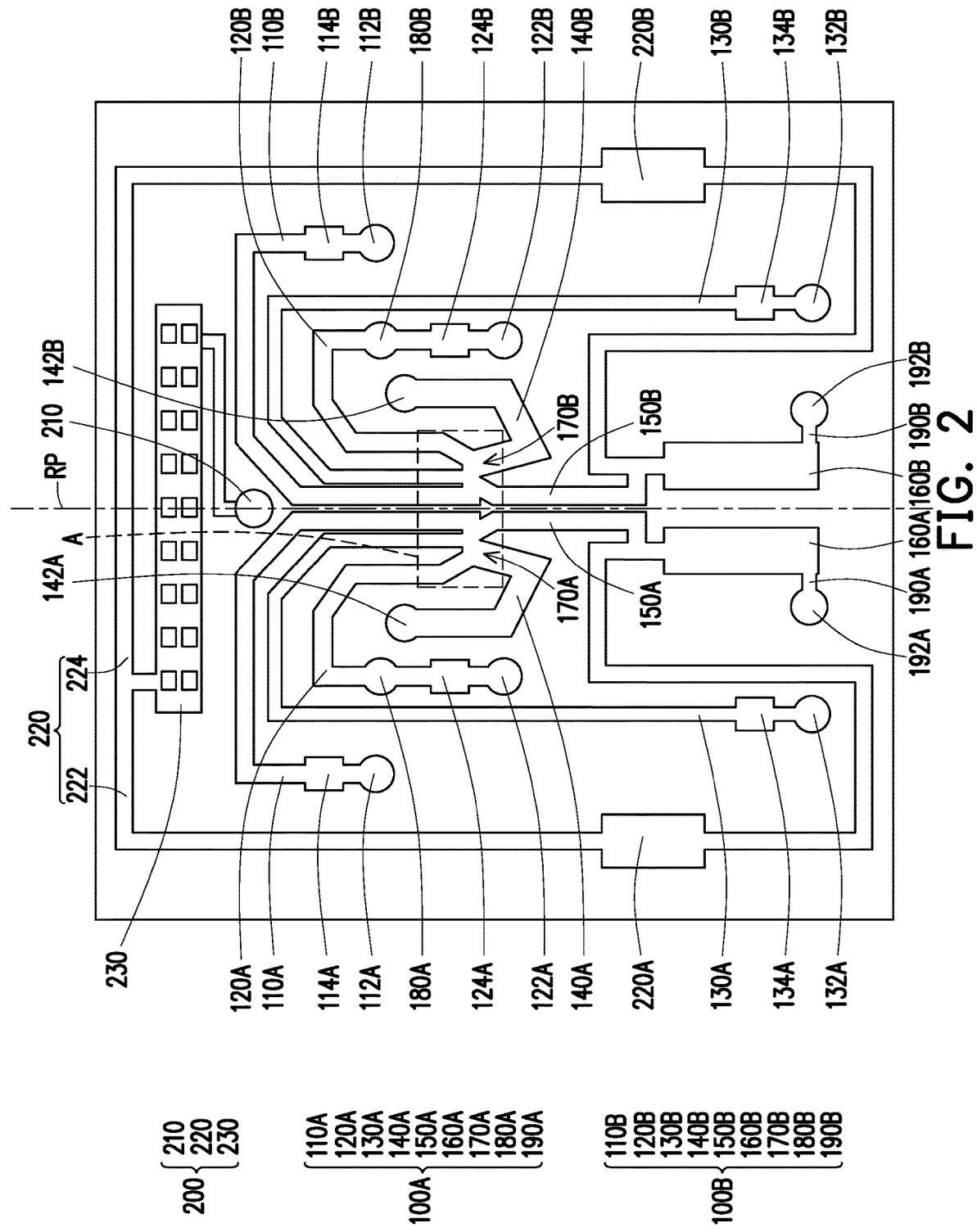
FIG. 2 schematically illustrates a top view of a microfluidic chip in accordance with an embodiment of the disclosure.

FIG. 2 schematically illustrates a top view of a microfluidic chip in accordance with an embodiment of the disclosure. Referring to FIG. 2, a microfluidic chip 10 includes a first cells enrichment system 100A and a second cells enrichment system 100B. The microfluidic chip 10 may have a cross sectional structure similar to that illustrated in FIG. 1, but not limited thereto. The first cells enrichment system 100A and the second cells enrichment system 100B may be used for conveying different sample fluids respectively; namely, the sample fluid travelling in the first cells enrichment system 100A is not mixed with the sample fluid travelling in the second cells enrichment system 100B. Accordingly, the microfluidic chip 10 may be used for running two sample fluids simultaneously.

The first cells enrichment system 100A includes a first fluid channel 110A, a second fluid channel 120A, a sample channel 130A positioned between the first fluid channel 110A and the second fluid channel 120A, a waste channel 140A, an inlet channel 150A, and a filtration chamber 160A reached by the inlet channel 150A. The first fluid channel 110A, the second fluid channel 120A and the sample channel 130A merge into a confluence chamber 170A, and the waste channel 140A and the inlet channel 150A diverge from the confluence chamber 170A. The inlet channel 150A forms a fluid communication between the filtration chamber 160A and the confluence chamber 170A.

In the first cells enriching system 100A, the first fluid channel 110A may have a first buffer inlet hole 112A at the terminal, and the first buffer inlet hole 112A is a hole passing through the outer surface of the microfluidic chip 10 and in fluid communication with the first fluid channel 110A. Specifically, the first buffer inlet hole 112A may be used for forming a fluid communication between the first fluid channel 110A and an external device such as a buffer fluid supply or the like. In addition, the first fluid channel 110A may further include a filter section 114A positioned between the first buffer inlet hole 112A and the joint of the first fluid channel 110A connecting to the confluence chamber 170A, such that a buffer fluid injected into the first fluid channel 110A through the first buffer inlet hole 112A may be filtered before entering the confluence chamber 170A and dust or contaminations in the buffer fluid may be prevented from entering the confluence chamber 170A.

The second fluid channel 120A may have a second buffer inlet hole 122A at the terminal, and the second buffer inlet hole 122A is a hole passing through the outer surface of the microfluidic chip 10 and in fluid communication with the second fluid channel 120A. Specifically, the second buffer inlet hole 122A may be used for forming a fluid communication between the second fluid channel 120A and an external device such as a buffer fluid supply or the like. In addition, the second fluid channel 120A may further include a filter section 124A positioned between the second buffer inlet hole 122A and the joint of the second fluid channel 120A connecting to the confluence chamber 170A, such that a buffer fluid injected into the second fluid channel 120A through the second buffer inlet hole 122A may be filtered before entering the confluence chamber 170A and dust or contaminations in the buffer fluid may be prevented from entering the confluence chamber 170A.

In the microfluidic chip 10, a buffer switching hole 180A may be further included in the first cells enriching system 100A. The buffer switching hole 180A is a hole passing through the outer surface of the microfluidic chip 10 and in communication with the second fluid channel 120A. The buffer switching hole 180A may be positioned between the second buffer inlet hole 122A and the joint of the second fluid channel 120A connecting to the confluence chamber 170A.

The sample channel 130A has a sample inlet hole 132A at the terminal, and the sample inlet hole 132A is a hole passing through the outer surface of the microfluidic chip 10 and in fluid communication with the sample channel 130A. The sample inlet hole 132A may be used for forming a fluid communication between the sample channel 130A and an external device such as a syringe or the like carrying a sample fluid. In an embodiment of the present invention, the sample fluid is a whole blood sample. In addition, the sample inlet hole 132A may further include a filter section 134A positioned between the sample inlet hole 132A and the joint of the sample channel 130A connecting to the confluence chamber 170A, such that a sample fluid injected into the sample channel 130A via the sample inlet hole 132A may be filtered before entering the confluence chamber 170A and blood clots, dust, or contaminations in the sample fluid may be prevented from entering the confluence chamber 170A.

In the first cells enriching system 100A, the sample channel 130A, the first fluid channel 110A and the second fluid channel 120A may be coplanar and the first fluid channel 110A and the second fluid channel 120A are arranged at opposite sides of sample channel 130A, such that the joint of the sample channel 130A connecting to the confluence chamber 170A may be positioned between the joint of the first fluid channel 110A connecting to the confluence chamber 170A and the joint of the second fluid channel 120A connecting to the confluence chamber 170A.

The waste channel 140A has a waste outlet hole 142A at the terminal, and the waste outlet hole 142A is a hole passing through the outer surface of the microfluidic chip 10 and in fluid communication with the waste channel 140A. The waste outlet hole 142A may be used for forming a fluid communication between the waste channel 140A and an external device or environment, such that the fluid in the confluence chamber 170A may be drained away from the microfluidic chip 10 via the waste channel 140A with the waste outlet hole 142A at the end.

The inlet channel 150A and the waste channel 140 are both positioned at the downstream side of the confluence chamber 170A. Specifically, the joint of the inlet channel 150A connecting to the confluence chamber 170A may be positioned corresponding to the joint of the first fluid channel 110A connecting to the confluence chamber 170A and the joint of the waste channel 140A connecting to the confluence chamber 170A may be positioned corresponding to the joint of the second fluid channel 120A connecting to the confluence chamber 170A. For example, the joint of the inlet channel 150A connecting to the confluence chamber 170A is closer to the reflection plane RP than the joint of the waste channel 140A connecting to the confluence chamber 170A when the joint of the first fluid channel 110A connecting to the confluence chamber 170A is closer to the reflection plane RP than the joint of the second fluid channel 120A connecting to the confluence chamber 170A. Alternatively, the joint of the inlet channel 150A connecting to the confluence chamber 170A may be further from the reflection plane RP than the joint of the waste channel 140A connecting to the confluence chamber 170A when the joint of the first fluid channel 110A connecting to the confluence chamber 170A is further from the reflection plane RP than the joint of the second fluid channel 120A connecting to the confluence chamber 170A.

The first cells enriching system 100A further includes an outlet channel 190A departs from the filtration chamber 160A. The outlet channel 190A may have an outlet hole 192A at the terminal, and the outlet hole 192A is a hole passing through the outer surface of the microfluidic chip 10 and in fluid communication with the outlet channel 190A. The outlet channel 190A with the outlet hole 192A at the end forms a fluid communication between the filtration chamber 160A and an external device or environment, such that the fluid in the filtration chamber 160A may be drained away from the microfluidic chip 10.

In the embodiment, the fluids including the sample fluid from the sample channel 130A and the buffer fluids from the first fluid channel 110A and the second fluid channel 120A may be injected into the microfluidic chip 10 via the inlet holes 132A, 112A, and 122A and drained away from the microfluidic chip 10 via the outlet holes 142A and 192A. When considering the flow direction of the fluids passing through the confluence chamber 170A during a cells enrichment operation using the microfluidic chip 10, the first side of the confluence chamber 170A and the second side of the confluence chamber 170A may be an upstream side and a downstream side respectively and may be opposite to each other.

The second cells enrichment system 100B includes a first fluid channel 110B, a second fluid channel 120B, a sample channel 130B positioned between the first fluid channel 110B and the second fluid channel 120B, a waste channel 140B, an inlet channel 150B, and a filtration chamber 160B reached by the inlet channel 150B. The first fluid channel 110B, the second fluid channel 120B and the sample channel 130B merge into a confluence chamber 170B, and the waste channel 140B and the inlet channel 150B diverge from the confluence chamber 170B. The inlet channel 150B forms a fluid communication between the filtration chamber 160B and the confluence chamber 170B.

The components of the second cells enrichment system 100B may be the same as the components of the first cells enrichment system 100A, and thus in the two systems, similar components are indicated by similar reference numbers. Specifically, the second cells enrichment system 100B may further include a first buffer inlet hole 112B at the end of the first fluid channel 110B, a filter section 114B in the first fluid channel 110B, a second buffer inlet hole 122B at the end of the second fluid channel 120B, a filter section 124B in the second fluid channel 120B, a buffer switching hole 180B in fluid communication with the second fluid channel 120B, a sample inlet hole 132B at the end of the sample channel 130B, a filter section 134B in the sample channel 130B, a waste outlet hole 142B at the end of the waste channel 140B, an outlet channel 190B departing from the filtration chamber 160B, and an outlet hole 192B at the end of the outlet channel 190B.

In the embodiment, the microfluidic chip 10 may have a bilateral symmetry configuration. For example, a channel layout of the first cells enrichment system 100A and a channel layout of the second cells enrichment system 100B are symmetric with respect to a reflection plane RP vertical to the microfluidic chip 10. Accordingly, the disposition relationship of the first fluid channel 110B, the second fluid channel 120B, the sample channel 130B, the waste channel 140B, the inlet channel 150B, the filtration chamber 160B, the confluence chamber 170B, the buffer switching hole 180B and the outlet channel 190B is a mirror symmetry of the disposition relationship of the first fluid channel 110A, the second fluid channel 120A, the sample channel 130A, the waste channel 140A, the inlet channel 150A, the filtration chamber 160A, the confluence chamber 170A, the buffer switching hole 180A and the outlet channel 190A. In some alternative embodiments, the channel layout of the first cells enrichment system 100A and the channel layout of the second cells enrichment system 100B may be partially symmetric with respect to the reflection plane RP.

In the present embodiment, the microfluidic chip 10 may further include a reagent system 200 shared by the first cells enrichment system 100A and the second cells enrichment system 100B. The reagent system 200, for example, includes reagent inlet 210, a reagent channel 220 and a bubble trapping chamber 230. The reagent channel 220 bifurcates in a first branch 222 and a second branch 224. The first branch 222 is in fluid communication with the filtration chamber 160A of the first cells enrichment system 100A, and the second branch 224 is in fluid communication with the filtration chamber 160B of the second cells enrichment system 100B. The bubble trapping chamber 230 is positioned between the reagent channel 220 and the reagent inlet 210. In some embodiments, the bubble trapping chamber 230 may be omitted and the reagent channel 220 may connect to the reagent inlet 210 without an intermediate structure. In addition, the first branch 222 and the second branch 224 of the reagent channel 220 may include an anti-contamination section 220A and an anti-contamination section 220B respectively. The anti-contamination section 220A or 220B may have a plurality of filter slits arranged therein, such that particles may be trapped at the anti-contamination section 220A or 220B. The filtration chamber 160A and the filtration chamber 160B both are in fluid communication with the reagent channel 220, such that it is possible that the particles or cells collected in the filtration chamber 160A and/or the filtration chamber 160B may travel to the reagent channel 220, which may cause a contamination between the first cells enrichment system 100A and the second cells enrichment system 100B. However, the particles or cells collected in the filtration chamber 160A or 160B would be trapped in the anti-contamination section 220A or 220B, which prevents from the contamination between the first cells enrichment system 100A and the second cells enrichment system 100B. In other words, though the first cells enrichment system 100A and the second cells enrichment system 100B share one reagent system 200, the contamination between the first cells enrichment system 100A and the second cells enrichment system 100B may be unlikely to happen.

Figure 3:
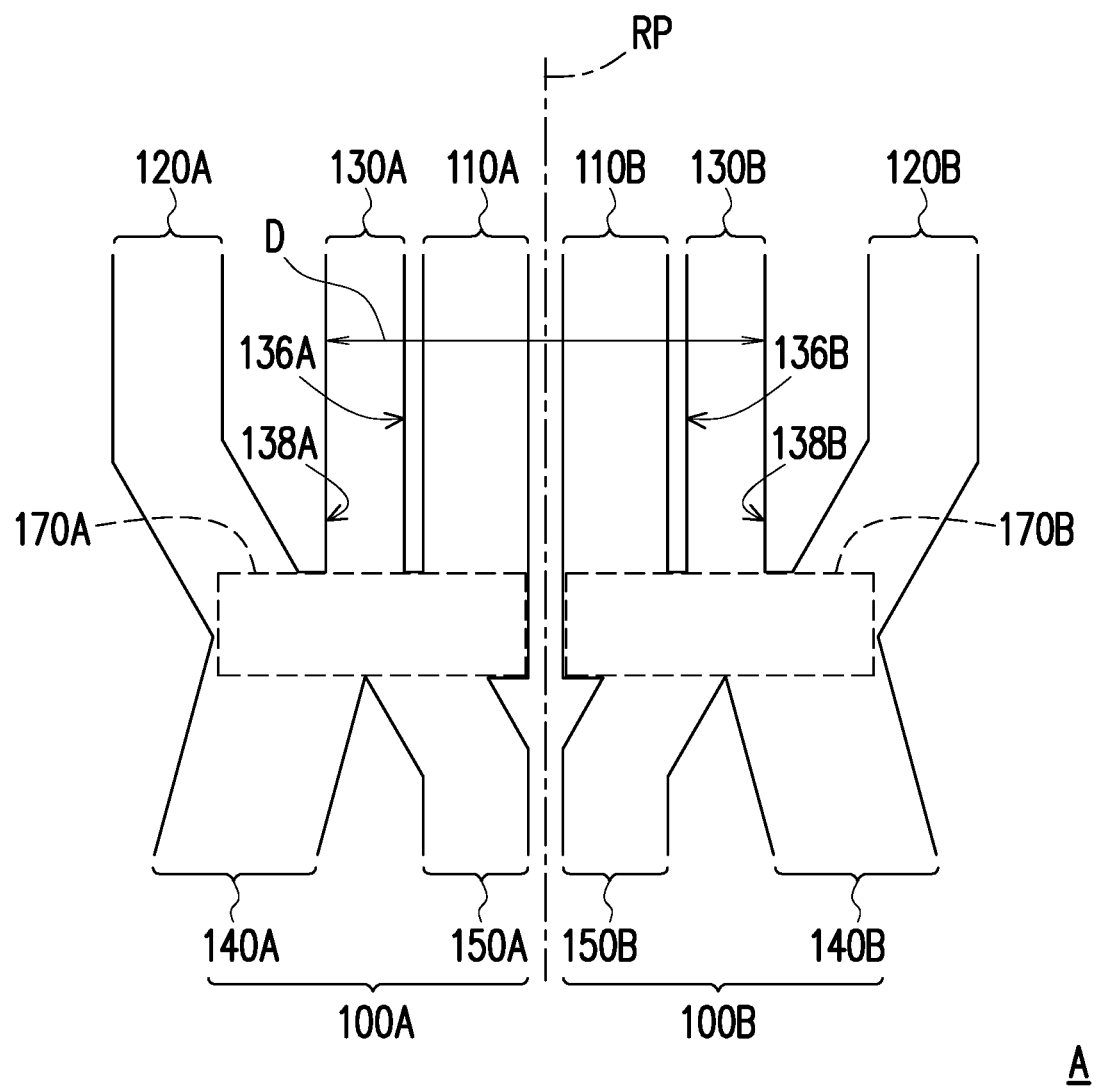
FIG. 3 schematically illustrates an enlarged view of a region A of the microfluidic chip in FIG. 2.

FIG. 3 schematically illustrates an enlarged view of a region A of the microfluidic chip in FIG. 2. As shown in FIG. 3, the sample channel 130A of the first cells enrichment system 100A has a first inner wall 136A and a first outer wall 138A. The sample channel 130B of the second cells enrichment system 100B has a second inner wall 136B and a second outer wall 138B. The first outer wall 138A and the second outer wall 138B are both far from the reflection plane RP. At the region proximate to the respective confluence chambers 170A/170B, the so-called outer wall 138A/138B of the sample channel 130A/130B in the embodiment represents the wall further from the reflection plane RP than the so-called inner wall 136A/136B. In addition, at the region proximate to the respective confluence chambers 170A/170B, a distance D between the first outer wall 138A and the second outer wall 138B is in the range from about 10 μm to about 1 cm. The skilled person in the art shall know that the distance D may be determined based on the view field size of the cell detector detecting the sample fluid in the microfluidic chip 10. In a preferred example, the distance D may be in the range from about 700 μm to 1200 μm. In some further alternative embodiments, the sample channel 130A and the sample channel 130B may be monitored by using different detectors, such that the distance D may not be determined based on the view filed size of the detector, but other considerations.

Figure 4A:
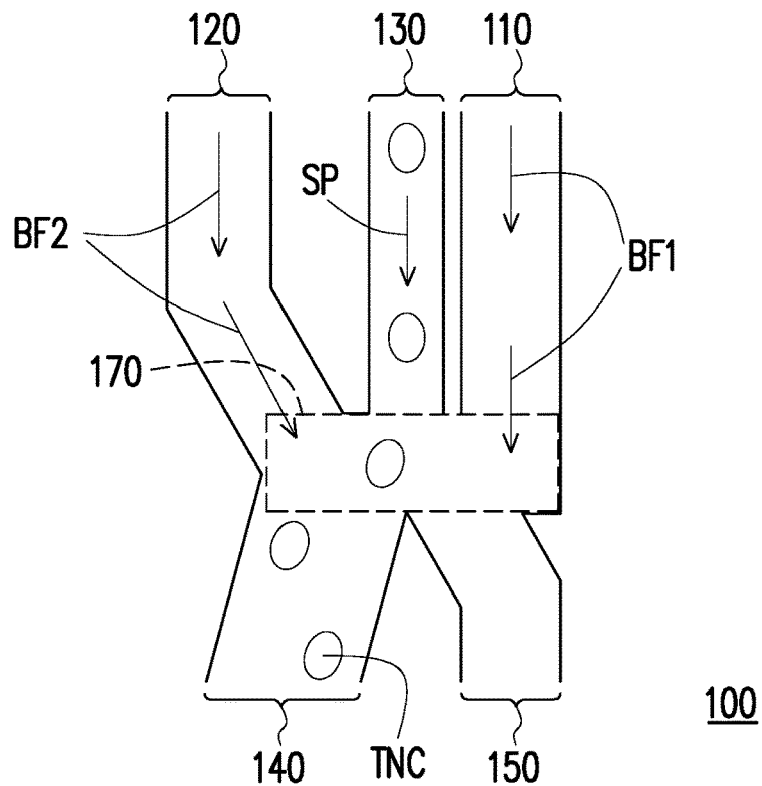
FIGS. 4A and 4B schematically illustrate an enlarged portion of one cells enrichment system.
Figure 4B:
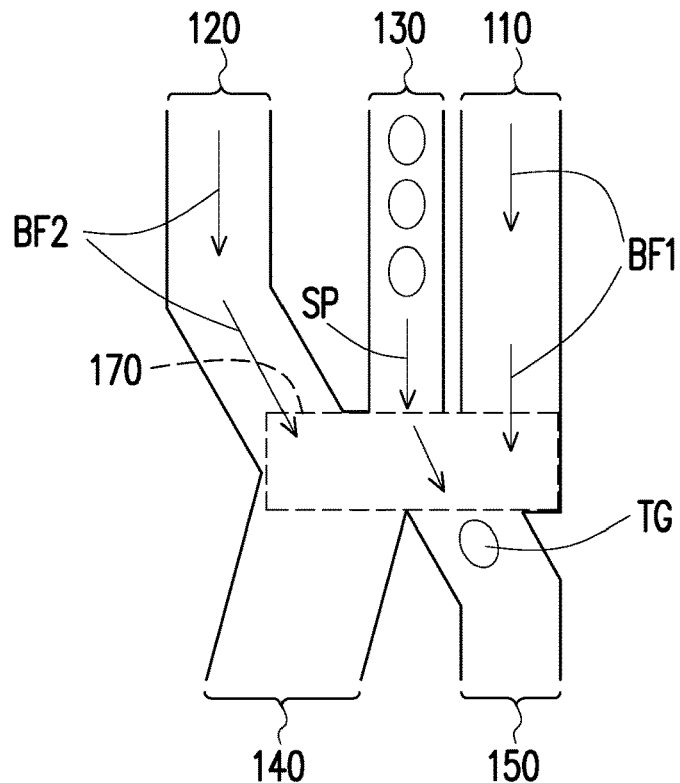

FIGS. 4A and 4B schematically illustrate an enlarged portion and the cells enrichment operation process in one of the cells enrichment system of the microfluidic chip 10. The cells enrichment system 100 is used for enriching target cells and particularly, sorting and enriching target cells in the microfluidic chip. During the cells enrichment operation, a first buffer fluid BF1 is supplied to the first fluid channel 110 and a second buffer fluid BF2 is supplied to the second fluid channel 120. In the embodiment, the first buffer fluid BF1 and the second buffer fluid BF2 may have the same composition, but not limited thereto. A sample fluid SP is injected to the sample channel 130 when the first buffer fluid BF1 and the second buffer fluid BF2 are continuously supplied. Therefore, the sample fluid SP, the first buffer fluid BF1 and the second buffer fluid BF2 all enter the confluence chamber 170 of the cells enrichment system 100. In the confluence chamber 170, the sample fluid SP may interpose between the first buffer fluid BF1 and the second buffer fluid BF2. By controlling the flow rates of the first buffer fluid BF1 and the second buffer fluid BF2, the sample fluid SP may be directed to enter one of the waste channel 140 and the inlet channel 150. Therefore, the cells enrichment system 100 may perform two operation modes.

The sample fluid SP may be a blood sample having cells (the non-target cell TNC denoted in FIG. 4A and the target cell TG denoted in FIG. 4B) therein. In one mode as shown in FIG. 4A, the flow rate of the first buffer fluid BF1 may be equal to or greater than the flow rate of the second buffer fluid BF2 such that the sample fluid SP in the confluence chamber 170 may be directed to enter the waste channel 140. In another mode as shown in FIG. 4B, at least one of the flow rates of the first buffer fluid BF1 and the second buffer fluid BF2 is adjusted to render the flow rate of the first buffer fluid BF1 smaller than the flow rate of the second buffer fluid BF2, which directs the sample fluid SP in the confluence chamber 170 entering the inlet channel 150. By using this operation in each of the first and the second cells enrichment systems 100A and 100B of the microfluidic chip 10 in FIG. 2, the sample fluid SP entering the waste channel 140 may be drained away from the chip and the sample fluid SP entering the inlet channel 150 may further convey to the filtration chamber to be enriched therein. During the cells enrichment operation, a target cell detection step may be carried out and the target cell detection step may distinguish the non-target cells TNC and the target cells TG in the sample fluid SP. The mode of FIG. 4A may be performed when no target cells TG is detected and the mode of FIG. 4B may be performed upon a detection of the target cell TG in the sample fluid, such that the non-target cells TNC may be drained away from the waste channel 140 and the target cell TG may enter the inlet channel 150 and be sorted and enriched in the chip. Accordingly, the sample fluid SP may be sorted before being collected in the chip.

In one instance, a flow rate of the sample fluid SP travelling in the sample channel 130 may be 65 μl/min. In some alternative embodiments, a flow rate of the sample fluid SP travelling in the sample channel 130 may be controlled so that a time of the sample fluid SP travelling to the confluence chamber 170 after being injected to the sample channel 130 may be less than 1 ms. Under the mode of FIG. 4A, according to a preferred embodiment, a flow rate of the first buffer fluid BF1 travelling in the first fluid channel 110 may be about 150 μl/min and a flow rate of the second buffer fluid BF2 travelling in the second fluid channel 120 may be about 135 μl/min, which allows to direct the sample fluid SP entering the waste channel 140 from the confluence chamber 170. Under the mode of FIG. 4B, according to a preferred embodiment, a flow rate of the first buffer fluid BF1 travelling in the first fluid channel 110 may be about 99 μl/min and a flow rate of the second buffer fluid BF2 travelling in the second fluid channel 120 may be about 600 μl/min, which allows to direct the sample fluid SP entering the inlet channel 150 from the confluence chamber 170. However, the disclosure is not limited to the above flow rate values. Generally, the flow rate of the fluid travelling in each channel may be modified based on the design requirement; for example, the flow rate of the fluid travelling in each channel may be in the range of 10 μl/min to 1,000 μl/min.

In addition, the cells enrichment operation shown in FIGS. 4A and 4B may be performed independently in the first and the second cells enrichment systems 100A and 100B of the microfluidic chip 10. Namely, the sample fluid injected to the sample channel of the first cells enrichment system 100A and the sample fluid injected to the sample channel of the second cells enrichment system 100B are different. Therefore, different modes may be performed in the first cells enrichment system 100A and the second cells enrichment system 100B at the same time.

Figure 5:
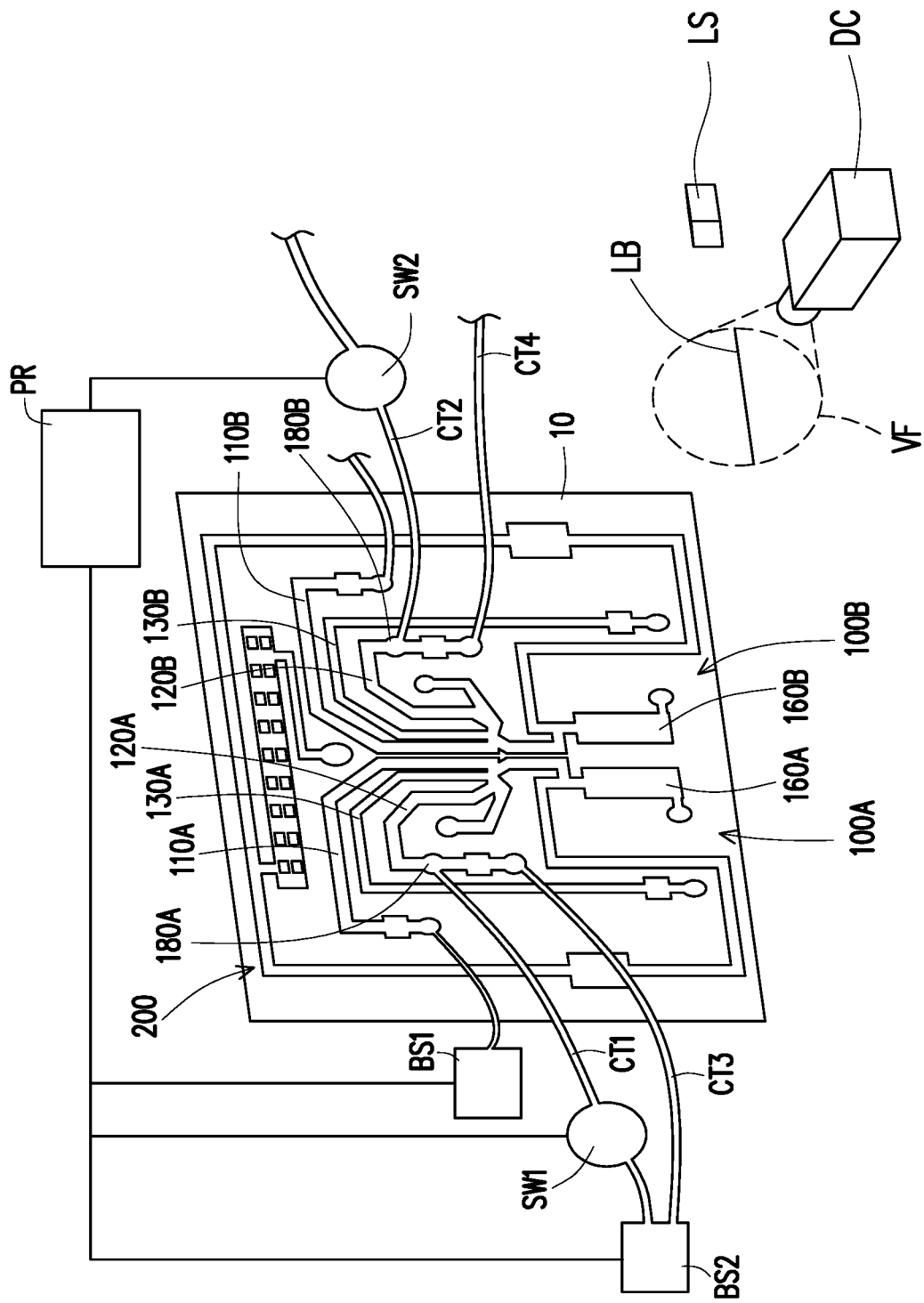
FIG. 5 schematically illustrates an apparatus for enriching cells in accordance with an embodiment of the disclosure.

FIG. 5 schematically illustrates an apparatus for enriching cells in accordance with an embodiment of the disclosure. The microfluidic chip 10 have the channel layout as shown in FIG. 2 and some reference numbers are omitted in FIG. 5 for clearly illustrate the apparatus in the embodiment. Therefore, the detail structure of the microfluidic chip 10 may refer to the related descriptions of FIG. 2. The apparatus 1000 shown in FIG. 5 includes a microfluidic chip 10, two switches SW1 and SW2, a first buffer supply BS1, a second buffer supply BS2, and connecting tubes such as CT1, CT2, CT3 and CT4. The switch SW1 is connected to the second fluid channel 120A of the first cells enrichment system 100A and the second switch SW2 is connected to the second fluid channel 120B of the second cells enrichment system 100B. Specifically, the switch SW1 is attached to a connecting tube CT1 inserting to the buffer switching hole 180A so as to be connected to the second fluid channel 120A and the switch SW2 is attached to a connecting tube CT2 inserting to the buffer switching hole 180B so as to be connected to the second fluid channel 120B. In some embodiments, each of the switch SW1 and the switch SW2 may be a valve which allows a fluid passing through the connecting tube CT1 or CT2 at an "on" or "activated" state and prohibits the fluid passing through the connecting tube CT1 or CT2 at an "off" or "non-activated" state.

The first buffer supply BS1 may be in fluid communication with the first fluid channel 110A of the first cells enrichment system 100A and the first fluid channel 110B of the second cells enrichment system 100B via different connecting tubes. For illustrating the apparatus 1000 clearly, some connecting tubes connecting to the second cells enrichment system 100B are omitted, but it is known that there is at least one connecting tube between the inlet hole of the first fluid channel 110B of the second cells enrichment system 100B and the first buffer supply BS1. The first buffer supply BS1 may supply a first buffer fluid to the first fluid channel 110A and the first fluid channel 110B independently so that the first buffer fluid travelling in the first fluid channel 110A and the first buffer fluid travelling in the first fluid channel 110B may be independently controlled. In some alternative embodiments, the first buffer fluid travelling in the first fluid channel 110A and the first buffer fluid travelling in the first fluid channel 110B may be supplied by different buffer supplies.

The second buffer supply BS2 is connected to the microfluidic chip 10 for supplying a second buffer fluid to the second fluid channel 120A of the first cells enrichment system 100A and the second fluid channel 120B of the second cells enrichment system 100B. For illustrating the apparatus 1000 clearly, the connecting tube CT2 connecting to the second cells enrichment system 100B is partially shown. Specifically, the second buffer supply BS2 is in fluid communication with the second fluid channel 120A via the connecting tube CT1 through the second buffer inlet hole 122A, and the connecting tube CT3 through the buffer switching hole 180A. Similarly, the second buffer supply BS2 is also in fluid communication with the second fluid channel 120E via the connecting tube CT2 through the second buffer inlet hole 122B, and the connecting tube CT4 through the buffer switching hole 180B. In some alternative embodiments, each of the connecting tubes CT1, CT2, CT3 and CT4 may be supplied by four different buffer supplies.

In the present embodiment, the apparatus 1000 may further include a cell detector DC. The cell detector DC may include a lens having a view field VF for monitoring the sample channel 130A of the first enrichment system 100A and the sample channel 130B of the second cells enrichment system 100B. In some embodiments, the size of the view field VF may be sufficient that both the sample channel 130A and the sample channel 130B are simultaneously viewed within the view field VF. However, in some alternative embodiment, the cell detector DC may monitor the sample channel 130A and the sample channel 130B independently under the view field VF by moving the position of the microfluidic chip 10.

The apparatus 1000 may further include a processor PR configured to control the switches SW1 and SW2, and the first and second buffer supplies BS1 and BS2. Specifically, under the mode of FIG. 4A, the processor PR may be configured to control the second buffer supply BS2 to form the buffer flow in the second fluid channel 120A or 120B, such that the buffer flow direct the sample fluid from the sample channel 130A or 130B to enter the waste channel 140A or 140B at the confluence chamber 170A or 170B. Under the mode of FIG. 4B, the processor PR is configured to control the first buffer supply BS1 and the second buffer supply BS2 and also activate the switch SW1 or SW2 to adjust the buffer flows in the second fluid channels 120A or 120B, such that the adjusted buffer flow in the second fluid channels 120A or 120B allows to direct the sample fluid from the sample channel 130A or 130B to enter the inlet channel 150A or 150B at the confluence chambers 170A or 170B.

Specifically, the apparatus 1000 may further include a light source LS. During the cells enrichment operation, the microfluidic chip 10 is placed under the cell detector DC in a manner allowing a portion of the sample channels 130A and 130B to be positioned within the view field VF of the cell detector DC. The light source LS is configured to irradiate a light beam LB on a portion of the microfluidic chip 10 within the view field VF of the cell detector DC. That is, a portion of the sample channels 130A and 130B and at least a portion of the light beam LB may be viewed simultaneously in the view field VF. The light beam LB may be a linear beam capable of distinguishing a target cell and a non-target cell. For example, the sample fluid may be mixed with a reagent before being injected into the sample channel 130A or 130B to administrate a fluorescent immunoassays. The fluorescent dyed target cells in the sample fluid travelling in the same channel 130A/130B may absorb light or energy at a specific wavelength provided by the light beam LB, and then emits light or energy at a different wavelength thus the user can determine whether a target cell exists in the sample fluid.

During the cells enrichment operation, the first buffer supply BS1 continuously supplies the first buffer fluid BF1 to the first cells enrichment system 100A and the second cells enrichment system 100B at a constant flow rate, and the second buffer supply BS2 also continuously supplies the second buffer fluid BF2 through the connection tube CT3 or CT4 to the first cells enrichment system 100A and the second cells enrichment system 100B at a constant flow rate. Under the mode of FIG. 4A, if no target cell is detected by the cell detector, the switch SW1 and SW2 is at "off" or "inactivate" status, so that there is no buffer fluid supplies to the connecting tubes CT1 and CT2. Therefore, the flow rate of BF1 may be equal to or greater than the flow rate of BF2, the sample fluid injected into the sample channels 130A or 130B enters the waste channel 140A or 140B from the confluence chamber 170A or 170B and is further drained away from the microfluidic chip 10 via the waste outlet hole 142A (denoted in FIG. 2).

Under the mode of FIG. 4B, once the target cell in the sample fluid of the sample channel 130A is detected, the processor controls the switch SW1 and the switch SW2 to change at "on" or "activated" status, then the buffer supply BS2 may supply buffer fluid through the CT1 and CT2 to increase the flow rate of the second buffer fluid BF2. Therefore, the flow rate of the first buffer fluid BF1 may be smaller than the flow rate of the second buffer fluid BF2, the adjusted flow of the buffer fluid travelling in the second fluid channel 120A may direct the sample fluid in the confluence chamber 170A to enter the inlet channel 150A.

In one preferred embodiment, the activating of the switch SW1 may last for a duration such as in a range from 1 ms to 200 ms. The skilled person in the art shall understand how to decide appropriate time interval according to different samples.

Owing that the first cells enrichment system 100A and the second cells enrichment system 100B are independently operated, different sample fluids may be sorted independently and the target cells in the sample fluids may be separately collected and enriched in the first cells enrichment system 100A and the second cells enrichment system 100B to provide a high efficient cells enrichment operation.

In the apparatus 1000, a reagent for identification is further injected to the reagent system 200, such that the reagent for identification may enter the filtration chambers 160A and 160B. The reagent for identification may further identify the cells collected in the filtration chambers 160A and 160B, such that the ghost target cells and the real target cells collected in the filtration chambers 160A and 160B may be distinguished. In the embodiment, two sample fluids may be respectively run in the first cells enrichment system 100A and the second cells enrichment system 100B while one reagent system 200 is shared by the first cells enrichment system 100A and the second cells enrichment system 100B, the contamination between the first cells enrichment system 100A and the second cells enrichment system 100B may be unlikely to happen by the configuration of the anti-contamination sections 220A and 220B (denoted in FIG. 2).

Figure 6:
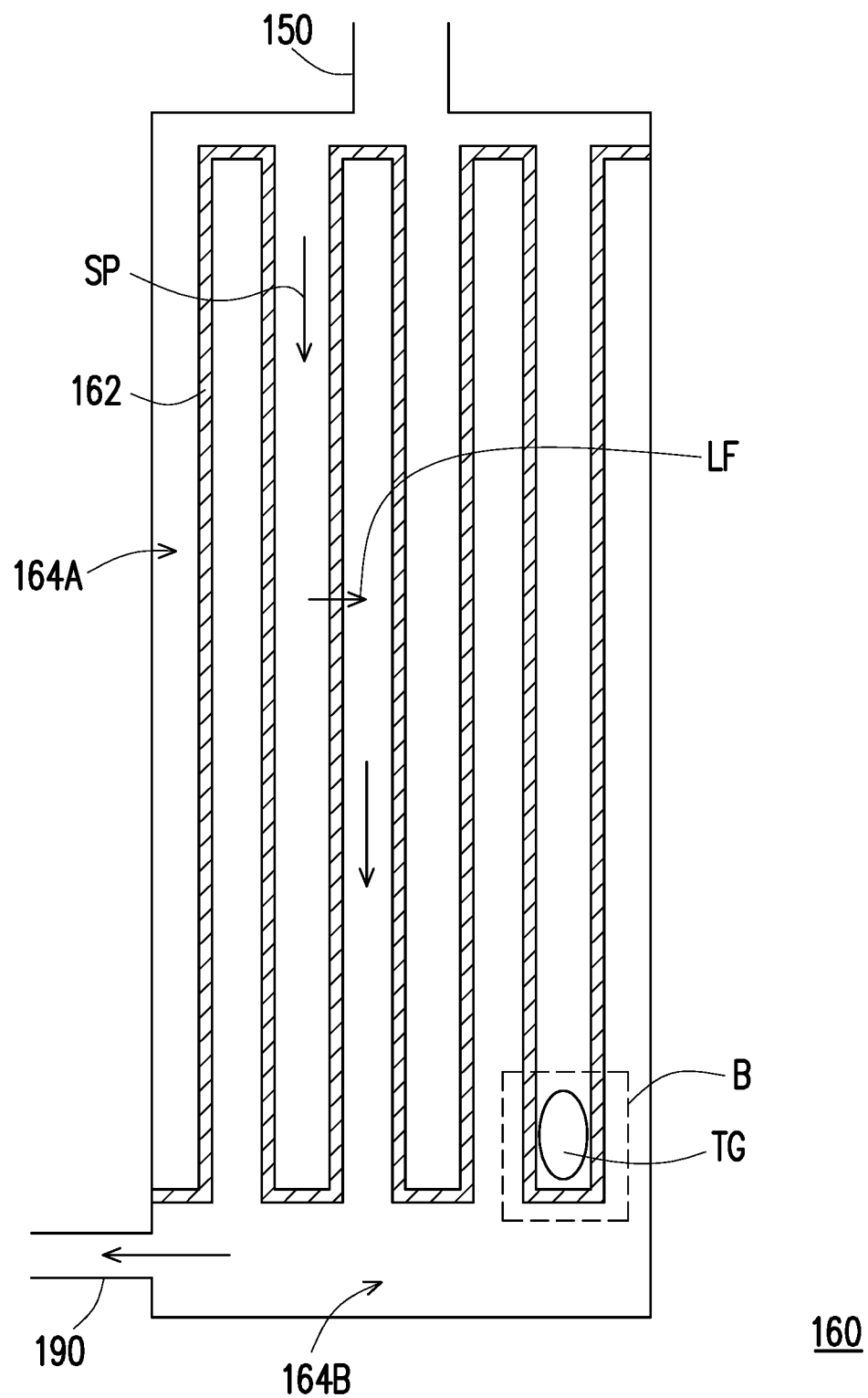
FIG. 6 schematically illustrates a filtration chamber in the cells enrichment system of a microfluidic chip in accordance with an embodiment of the disclosure.

FIG. 6 schematically illustrates a filtration chamber in the cells enrichment system of a microfluidic chip in accordance with an embodiment of the disclosure. Referring to FIG. 6, the filtration chamber 160 in the present embodiment may be connected between an inlet channel 150 and an outlet channel 190 and may be an exemplary example of the filtration chamber 160A or 160B of the microfluidic chip 10 shown in FIG. 2. The filtration chamber 160 includes a filtration wall 162 disposed within the filtration chamber 160 and the filtration wall 162 splits the filtration chamber 160 into a first sub-chamber 164A and a second sub-chamber 164B. The filtration wall 162 may be meandered in the filtration chamber 160. The sample fluid SP may enter the filtration chamber 160 from the inlet channel 150 and the filtration wall 162 may block the sorted target cells TG in the sample fluid SP to collect the sorted target cells TG in the first sub-chamber 164A. The liquid flow LF of the sample fluid SP may pass through the filtration wall 162 and enter the second sub-chamber 164B. Finally, the liquid flow LF of the sample fluid SP may leave from the filtration chamber 160 to the outlet channel 190 and be further drained away from the microfluidic chip via the outlet hole at the end of the outlet channel 190.

Figure 7:
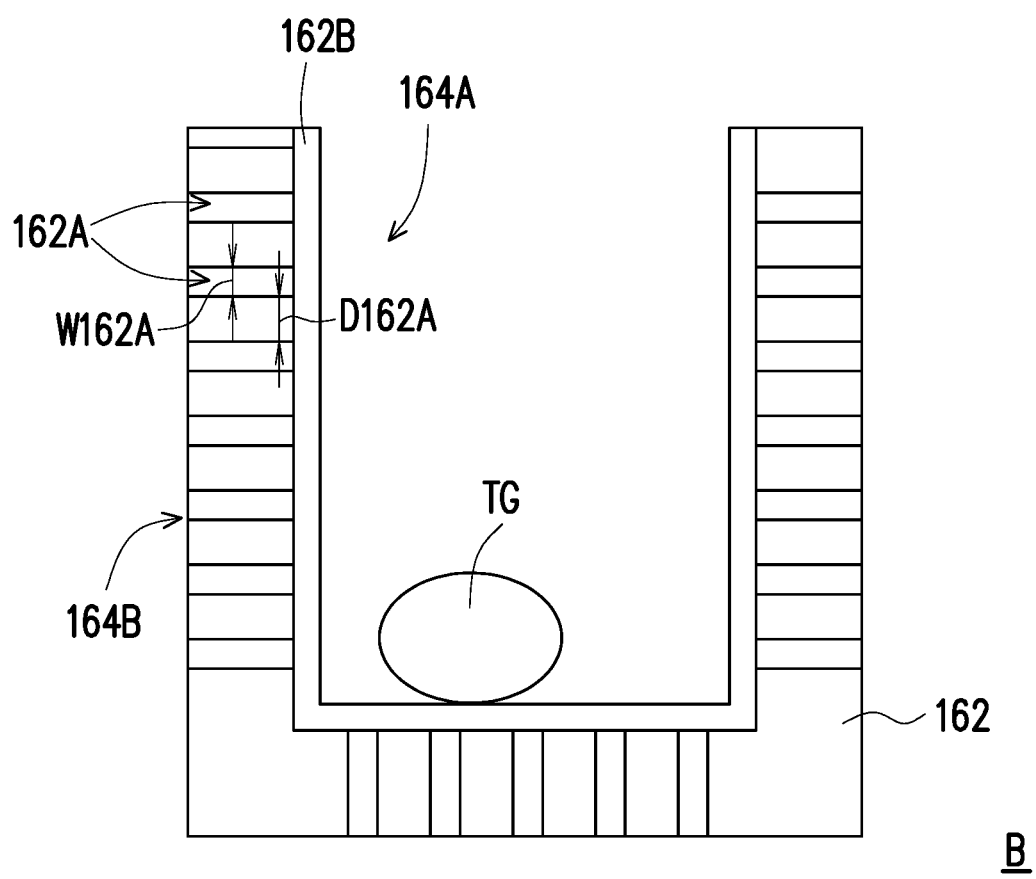
FIG. 7 schematically illustrates an enlarged portion B of the filtration wall depicted in FIG. 6.

FIG. 7 schematically illustrates an enlarged portion B of the filtration wall depicted in FIG. 6. Referring to FIGS. 6 and 7, the filtration wall 162 includes a plurality of through slits 162A. Each of the plurality of through slits 162A crosses through the filtration wall 162 to form a fluid communication between the first sub-chamber 164A and the second sub-chamber 164B. In some embodiments, a width W162A of each of the through silts 162A may be 5 μm, a distance D162A between two adjacent through slits 162A may be 10 μm and the filtration wall 162 may have 100 to 100,000 through silts 162A arranged therein. In addition, the total length of the filtration wall 162 may be determined based on the design requirement.

Figure 8:
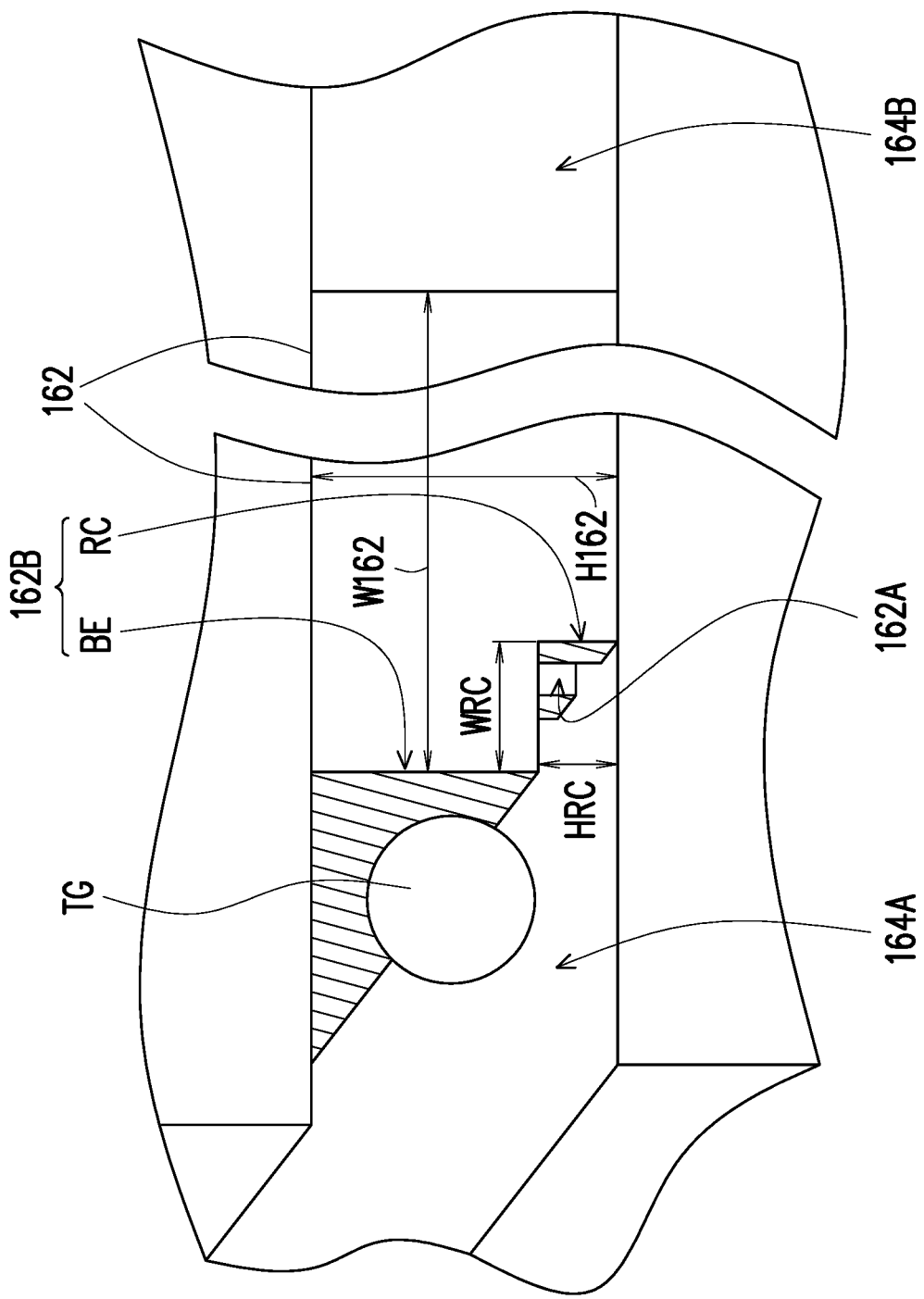
FIG. 8 schematically illustrates an enlarged perspective view of a portion of the filtration wall.

FIG. 8 schematically illustrates an enlarged perspective view of a portion of the filtration wall. Referring to FIGS. 6, 7 and 8, the filtration wall 162 dividing the first sub-chamber 164A and the second sub-chamber 164B may further include a roof-like structure 162B arranged at a side of the filtration wall 162 facing the first sub-chamber 164A. The roof-like structure 162B may be arranged between the through slits 162A and the first sub-chamber 164A as shown in FIG. 7. The roof-like structure 162B defines a blocking edge BE and a recess RC indented from the blocking edge BE. In some embodiments, the height HRC of the recess RC is smaller than the height H162 of the filtration wall 162 and the width WRC of the recess RC is smaller than the width W162 of the filtration wall 162. For example, the height HRC of the recess RC and the width WRC of the recess RC may be determined based on the requirement and the design of the cells enrichment operation. For example, if the sample fluid for the cells enrichment operation is a whole blood sample and the red blood cells need to be filtered by the through slits 162A, the height HRC of the recess RC may be 5 μm and the width WRC of the recess RC may be 10 μm.

The blocking edge BE is able to block the sorted target cell TG in the first sub-chamber 164A. Each of the through slits 162A is opened at the recess RC so that the sorted target cell TG leaning against the blocking edge BE may not close or block the through slits 162A. Accordingly, though the sorted target cell TG is leant against the filtration wall 162, the fluid communication between the first sub-chamber 164A and the second sub-chamber 164B is smooth and easy via the through slits 162A. In addition, the sorted target cell TG may maintain its shape without being deformed by the flow stress of the fluid travelling from the first sub-chamber 164A to the second sub-chamber 164B.

Figure 9:
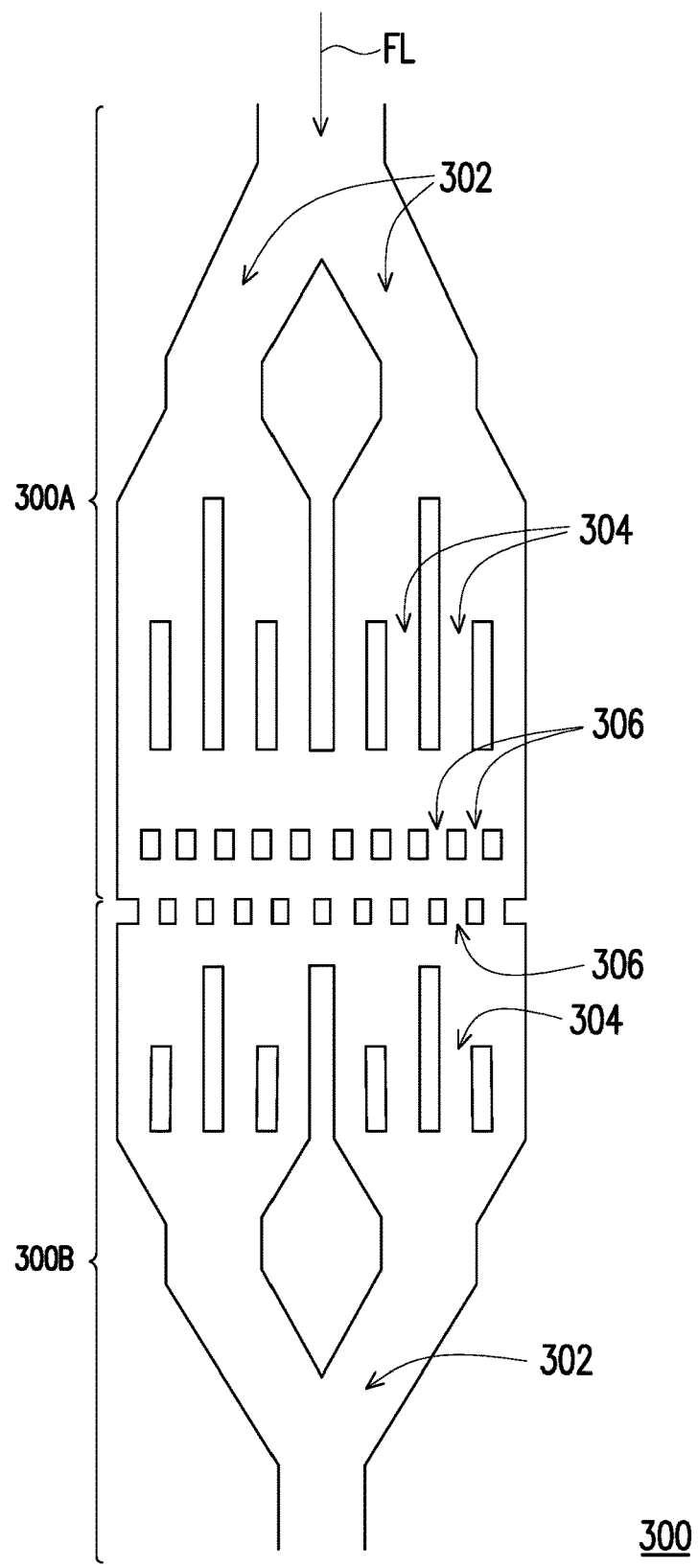
FIG. 9 schematically illustrates a filter structure in accordance with an embodiment of the disclosure.

FIG. 9 schematically illustrates a filter structure in accordance with an embodiment of the disclosure. Referring to FIG. 9, the filter structure 300 may be an exemplary structure of the filter sections 114A, 114B, 124A, 124B, 134A and 134B and the anti-contamination sections 220A and 220B in the microfluidic chip 10 of FIG. 2. The filter structure 300 may have a first portion 300A and a second portion 300B. Each of the first portion 300A and the second portion 300B includes a plurality of filter slits 302, a plurality of filter slits 304 and a plurality of filter slits 306. The fluid FL entering the filter structure 300 may firstly be separated into two sub-flows by the filter slits 302 of the first portion 300A, each sub-flow travelling in the filter slits 302 of the first portion 300A may further be separated into two sub-flows by the filter slits 304 of the first portion 300A, and each sub-flow travelling in the filter slits 304 of the first portion 300A may further be separated into two sub-flows by the filter slits 306 of the first portion 300A. The sub-flows travelling in the filter slits 306 of the first portion 300A may sequentially pass the filter slits 306, the filter slits 304 and the filter slits 302 of the second portion 300B. Accordingly, the particles or the large contaminations in the fluid FL may hardly pass through the filter structure 300. In some embodiments, the width of each filter slits 304 may be 0.075 mm and a width of each filter slit 306 may be 0.05 mm. In addition, the position of the filter slit 306 of the second section 300B may not align with the filter slit 306 of the first section 300A, such that the particles passing through the filter slit 306 of the first section 300A may be blocked by the filter slit 306 of the second section 300B. For example, the position of the filter slit 306 of the second section 300B may be corresponding to one separation structure between two adjacent filter slits 306 of the first section 300A.

In view of the foregoing, the microfluidic chip in accordance with the embodiment of the disclosure has two independent cells enrichment systems arranged in a symmetric manner so that the cells enrichment operation of the microfluidic chip may be performed to run two samples simultaneously, which improves the efficiency of enriching cells. According to some embodiments, the cells in the microfluidic chip are sorted before being collected so that the cells enrichment using the apparatus and/or the method of the disclosure may have high enriching rate of the target cells. In some embodiments, the filtration wall of the filtration chamber in the cells enrichment system may have a roof-like structure to block the sorted cells before the through slits such that the fluid communication between two sub-chambers divided by the filtration wall may remain smooth and easy, which also helps to maintain the shape of the sorted cells.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A microfluidic chip comprising a first cells enrichment system and a second cells enrichment system, wherein a channel layout of the first cells enrichment system and a channel layout of the second cells enrichment system are symmetric with respect to a reflection plane vertical to the microfluidic chip, and wherein each of the first cells enrichment system and the second cells enrichment system comprises:
   a first fluid channel;
   a second fluid channel;
   a sample channel positioned between the first fluid channel and the second fluid channel;
   a waste channel;
   an inlet channel;
   a filtration chamber reached by the inlet channel, and
   a filtration wall disposed within the filtration chamber and splitting the filtration chamber into a first sub-chamber and a second sub-chamber, the filtration wall comprising:
      a plurality of through slits, each of the plurality of through slits crossing through the filtration wall to form a fluid communication between the first sub-chamber and the second sub-chamber, and
      an overhang structure arranged at a side of the filtration wall facing the first sub-chamber, wherein the first sub-chamber is located between the inlet channel and the second sub-chamber, the overhang structure defines a blocking edge and a recess indented from the blocking edge, and the blocking edge is protruded into the first sub-chamber,
   wherein the first fluid channel, the second fluid channel and the sample channel converge at a first side of a confluence chamber, the waste channel and the inlet channel diverge from a second side of the confluence chamber, the first side and the second side are opposite sides, and the inlet channel forms a fluid communication between the filtration chamber and the confluence chamber, and
   wherein the sample channel of the first cells enrichment system has a first inner wall and a first outer wall at a portion immediately upstream from the confluence chamber, the sample channel of the second cells enrichment system has a second inner wall and a second outer wall at a portion immediately upstream from the confluence chamber, the first outer wall and the second outer wall are both farther from the reflection plane than the first inner wall and the second inner wall respectively, and a distance between the first outer wall and the second outer wall is in the range from about 10 µm to about 1 cm.

2. The microfluidic chip of claim 1, wherein the distance between the first outer wall and the second outer wall is in the range from about 700 µm to about 1200 µm.

3. The microfluidic chip of claim 1, further comprising a reagent inlet and a reagent channel, wherein the reagent channel bifurcates in a first branch and a second branch, the first branch is in fluid communication with the filtration chamber of the first cells enrichment system, and the second branch is in fluid communication with the filtration chamber of the second cells enrichment system.

4. The microfluidic chip of claim 3, wherein each of the first branch and the second branch of the reagent channel comprises an anti-contamination section with a plurality of filter slits arranged therein.

5. The microfluidic chip of claim 3, wherein the reagent channel further comprises a bubble trapping chamber before bifurcating in the first branch and the second branch.

6. The microfluidic chip of claim 1, wherein each of the first cells enrichment system and the second cells enrichment system further comprises a waste outlet hole passing through an outer surface of the microfluidic chip and in fluid communication with the waste channel.

7. The microfluidic chip of claim 1, wherein each of the first cells enrichment system and the second cells enrichment system further comprises an outlet channel departing from the second sub-chamber.

8. The microfluidic chip of claim 7, wherein each of the first cells enrichment system and the second cells enrichment system further comprises an outlet hole passing through an outer surface of the microfluidic chip and in fluid communication with the outlet channel.

9. The microfluidic chip of claim 1, wherein each of the first cells enrichment system and the second cells enrichment system further comprises:
   a sample inlet hole passing through an outer surface of the microfluidic chip and in fluid communication with the sample channel;
   a first buffer inlet hole passing through the outer surface of the microfluidic chip and in fluid communication with the first fluid channel;
   a second buffer inlet hole passing through the outer surface of the microfluidic chip and in fluid communication with the second fluid channel; and a buffer switching hole passing through the outer surface of the microfluidic chip and in fluid communication with the second fluid channel between the second buffer inlet hole and the confluence chamber.

10. An apparatus for enriching cells, comprising:
a microfluidic chip comprising a first cells enrichment system and a second cells enrichment system, wherein a channel layout of the first cells enrichment system and a channel layout of the second cells enrichment system are symmetric with respect to a reflection plane vertical to the microfluidic chip, and each of the first cells enrichment system and the second cells enrichment system comprises:
a first fluid channel;
a second fluid channel;
a sample channel positioned between the first fluid channel and the second fluid channel;
a waste channel;
an inlet channel; and
a filtration chamber reached by the inlet channel, and
a filtration wall disposed within the filtration chamber and splitting the filtration chamber into a first sub-chamber and a second sub-chamber, the filtration wall comprising:
a plurality of through slits, each of the plurality of through slits crossing through the filtration wall to form a fluid communication between the first sub-chamber and the second sub-chamber, and
an overhang structure arranged at a side of the filtration wall facing the first sub-chamber, wherein the first sub-chamber is located between the inlet channel and the second sub-chamber, the overhang structure defines a blocking edge and a recess indented from the blocking edge, and the blocking edge is protruded into the first sub-chamber
wherein the first fluid channel, the second fluid channel and the sample channel converge at a first side of a confluence chamber, the waste channel and the inlet channel diverge from a second side of the confluence chamber, the first side and the second side are opposite sides, and the inlet channel forms a fluid communication between the filtration chamber and the confluence chamber, and wherein the sample channel of the first cells enrichment system has a first inner wall and a first outer wall at a portion immediately upstream from the confluence chamber, the sample channel of the second cells enrichment system has a second inner wall and a second outer wall at a portion immediately upstream from the confluence chamber, the first outer wall and the second outer wall are both farther from the reflection plane than the first inner wall and the second inner wall respectively, and a distance between the first outer wall and the second outer wall is in the range from about 10 μm to about 1 cm,
two switches respectively connected to the second fluid channel of the first cells enrichment system and the second fluid channel of the second cells enrichment system;
a cell detector having a view field, wherein the cell detector is configured to detect a target cell within the sample channels of the first cells enrichment system and the second cells enrichment system; and
a processor, configured to independently control the two switches in response to a detection result of the cell detector, wherein the processor, upon detection of the target cell within the sample channel of one of the first cells enrichment system and the second cells enrichment system, activates the corresponding switch connected to the one of the first cells enrichment system and the second cells enrichment system.

11. The apparatus for enriching cells of claim 10, further comprising:
a first buffer supply in fluid communication with the first fluid channel of each of the first cells enrichment system and the second cells enrichment system; and
a second buffer supply in fluid communication with the second fluid channel of each of the first cells enrichment system and the second cells enrichment system,
wherein one of the switches is connected between the second buffer supply and the second fluid channel of the first cells enrichment system and the other of the switches is connected between the second buffer supply and the second fluid channel of the second cells enrichment system,
wherein the processor is further configured to control the second buffer supply to form a buffer flow in the second fluid channel in each of the first cells enrichment system and the second cells enrichment system, and the buffer flow directs a sample fluid from the sample channel to enter the waste channel at the confluence chamber, and
wherein the processor, upon detection of the target cell, activates the corresponding switch to adjust the buffer flow, and the adjusted buffer flow directs the sample fluid from the sample channel to enter the inlet channel at the confluence chamber.

12. The apparatus for enriching cells of claim 10, wherein the microfluidic chip further comprises a reagent inlet and a reagent channel, and the reagent channel bifurcates in two branches respectively in fluid communication with the filtration chamber of the first cells enrichment system and the filtration chamber of the second cells enrichment system.

13. A method for enriching cells in a microfluidic chip, the microfluidic chip comprising a first cells enrichment system and a second cells enrichment system, wherein a channel layout of the first cells enrichment system and a channel layout of the second cells enrichment system are symmetric with respect to a reflection plane vertical to the microfluidic chip, and each of the first cells enrichment system and the second cells enrichment system comprises:
a first fluid channel;
a second fluid channel;
a sample channel positioned between the first fluid channel and the second fluid channel;
a waste channel;
an inlet channel; and
a filtration chamber reached by the inlet channel, and
a filtration wall disposed within the filtration chamber and splitting the filtration chamber into a first sub-chamber and a second sub-chamber, the filtration wall comprising:
a plurality of through slits, each of the plurality of through slits crossing through the filtration wall to form a fluid communication between the first sub-chamber and the second sub-chamber, and
an overhang structure arranged at a side of the filtration wall facing the first sub-chamber, wherein the first sub-chamber is located between the inlet channel and the second sub-chamber, the overhang structure defines a blocking edge and a recess indented from the blocking edge, and the blocking edge is protruded into the first sub-chamber, wherein the first fluid channel, the second fluid channel and the sample channel converge at a first side of a confluence chamber, the waste channel and the inlet channel diverge from a second side of the confluence chamber, the first side and the second side are opposite sides, and the inlet channel forms a fluid communication between the filtration chamber and the confluence chamber, and wherein the sample channel of the first cells enrichment system has a first inner wall and a first outer wall at a portion immediately upstream from the confluence chamber, the sample channel of the second cells enrichment system has a second inner wall and a second outer wall at a portion immediately upstream from the confluence chamber, the first outer wall and the second outer wall are both farther from the reflection plane than the first inner wall and the second wall respectively, and a distance between the first outer wall and the second outer wall is in the range from about 10 μm to about 1 cm, and the method comprising:

supplying a first buffer fluid to the first fluid channel of the first cells enrichment system and a second buffer fluid to the second fluid channel of the first cells enrichment system;

injecting a first sample fluid to the sample channel of the first cells enrichment system; and controlling the second buffer fluid in the second fluid channel of the first cells enrichment system to direct the first sample fluid to enter one of the waste channel and the inlet channel of the first cells enrichment system.

14. The method of claim 13, further comprising:

supplying the first buffer fluid to the first fluid channel of the second cells enrichment system and the second buffer fluid to the second fluid channel of the second cells enrichment system;

injecting a second sample fluid to the sample channel of the second cells enrichment system; and controlling the second buffer fluid in the second fluid channel of the second cells enrichment system to direct the second sample fluid from the sample channel of the second cells enrichment system to enter one of the waste channel and the inlet channel of the second cells enrichment system, wherein the controlling of the second buffer fluid in the second fluid channel of the second cells enrichment system is independent from the controlling of the second buffer fluid in the second fluid channel of the first cells enrichment system.

15. The method of claim 14, wherein the second buffer fluid in the second fluid channel of the second cells enrichment system is controlled to direct the second sample fluid from the sample channel of the second cells enrichment system to enter the inlet channel of the second cells enrichment system upon detection of a target cell within the sample channel of the second cells enrichment system.

16. The method of claim 13, wherein the second buffer fluid in the second fluid channel of the first cells enrichment system is controlled to direct the first sample fluid from the sample channel of the first cells enrichment system to enter the inlet channel of the first cells enrichment system upon detection of a target cell within the sample channel of the first cells enrichment system.

* * * * *